United States Patent [19]
Carlucci et al.

[11] Patent Number: 5,998,965
[45] Date of Patent: Dec. 7, 1999

[54] DIRECT PLUG IN POWER TOOL USING SINGLE PAIR OF CONTACTS FOR BOTH AC AND DC CURRENTS

[75] Inventors: Vito J. Carlucci; Harold R. Taylor, both of Stratford, Conn.

[73] Assignee: Conair Corporation, Stamford, Conn.

[21] Appl. No.: 09/059,543

[22] Filed: Apr. 13, 1998

[51] Int. Cl.⁶ ................................................. H01M 10/46
[52] U.S. Cl. ........................................ 320/111; 320/114
[58] Field of Search .................................. 320/111, 112, 320/114, 115, 138, FOR 155, FOR 160

[56] References Cited

U.S. PATENT DOCUMENTS

| | | |
|---|---|---|
| 3,316,417 | 4/1967 | Tolmie . |
| 3,525,912 | 8/1970 | Wallin . |
| 3,533,119 | 10/1970 | Dokos . |
| 3,685,080 | 8/1972 | Hubner . |
| 3,973,179 | 8/1976 | Weber et al. . |
| 4,084,280 | 4/1978 | May . |
| 4,374,354 | 2/1983 | Petrovic et al. . |
| 4,544,816 | 10/1985 | Benz . |
| 4,743,735 | 5/1988 | Abura et al. . |
| 4,827,552 | 5/1989 | Bojar et al. . |
| 5,170,525 | 12/1992 | Cafaro . |
| 5,268,629 | 12/1993 | Franke . |
| 5,553,675 | 9/1996 | Pitzen et al. . |
| 5,561,881 | 10/1996 | Klinger et al. . |
| 5,613,259 | 3/1997 | Craft et al. . |

*Primary Examiner*—Edward H. Tso
*Attorney, Agent, or Firm*—Ohlandt, Greeley, Ruggiero & Perle

[57] ABSTRACT

A cordless modular power tool having a battery module, a motor module and a tool module that can be a saw, drill, toothbrush, flosser and the like. First and second electrical plug units are situated on the battery and motor modules respectively. The battery module plug unit is used in a d.c. mode to supply d.c. current to the motor and in an a.c. mode to receive a.c. current for charging the battery. Switching between the two modes is accomplished during plugging and unplugging of the two modules by locating a magnet in the motor module which influences an actuator arm in battery module to do the switching.

13 Claims, 2 Drawing Sheets

DIRECT PLUG IN POWER TOOL USING SINGLE PAIR OF CONTACTS FOR BOTH AC AND DC CURRENTS

FIELD OF INVENTION

This invention relates to novel and improved modular power tool apparatus and in particular to a novel and improved cordless modular tool.

BACKGROUND OF INVENTION

Known cordless power tools came in a variety of assemble and play modules. In U.S. Pat. No. 4,374,354 the tool module, for example a toothbrush, fits into one end of a power module that contains both a d.c. motor and a battery. The other end of the power module fits into a battery recharge module that receives power from an a.c. power main. Although this unit contains electrical isolation of the motor and battery, the isolation can fail during recharge, resulting in damage to the motor.

Other cordless power tools solve the isolation failure problem by placing the motor and battery in separate modules. In U.S. Pat. Nos. 3,533,119 and 5,170,525 the battery module has both an a.c. plug unit and a d.c. plug unit. The a.c. plug unit is operable for recharge to plug directly into an a.c. main and the d.c. plug unit is unused and therefore an open circuit. The motor module also contains a mating d.c. plug unit which is active to receive battery current when plugged to the battery module d.c. plug unit. The motor module also includes an a.c. plug receptacle mounted in dielectric material so as to be electrically inactive when plugged with the a.c. plug unit of the battery module. That is, the a.c. plug units perform a purely mechanical coupling function during plug and play.

Although the cordless power tools disclosed in the aforementioned patents avoid the isolation problem during recharge, each requires numerous parts resulting in high cost.

An object of this invention is to provide a novel and improved cordless modular power tool.

Another object of this invention is to provide a cordless modular power tool that uses the same plug unit terminals for supplying d.c. current to the motor and for receiving a.c. current from an a.c. outlet for battery charging purposes.

SUMMARY OF THE INVENTION

Briefly, a cordless modular power tool embodying the invention includes a battery module containing a battery and a motor module containing a d.c. motor. First and second mating plug units are mounted on the battery and motor modules, respectively. Switch means are provided to place the first plug unit (i) in an a.c. mode when unplugged from the second plug unit so as to conduct a.c. current when plugged into an a.c. receptacle to charge the battery and (ii) in a d.c. mode when plugged into the second plug unit so as to conduct d.c. current from the battery to the motor via the second plug unit.

In the preferred embodiment, the switch means includes a switch that is activated during the process of being plugged for the d.c. mode and is deactivated during the process of being unplugged from the motor module for the a.c. mode. A switch actuator includes a permanent magnet and a steel arm that responds to the field of the magnet during the plugging and unplugging processes to activate and deactivate the switch.

BRIEF DESCRIPTION OF THE DRAWINGS

In the drawings, like reference characters denote like elements of structure

DESCRIPTION OF PREFERRED EMBODIMENT

Figure 1:
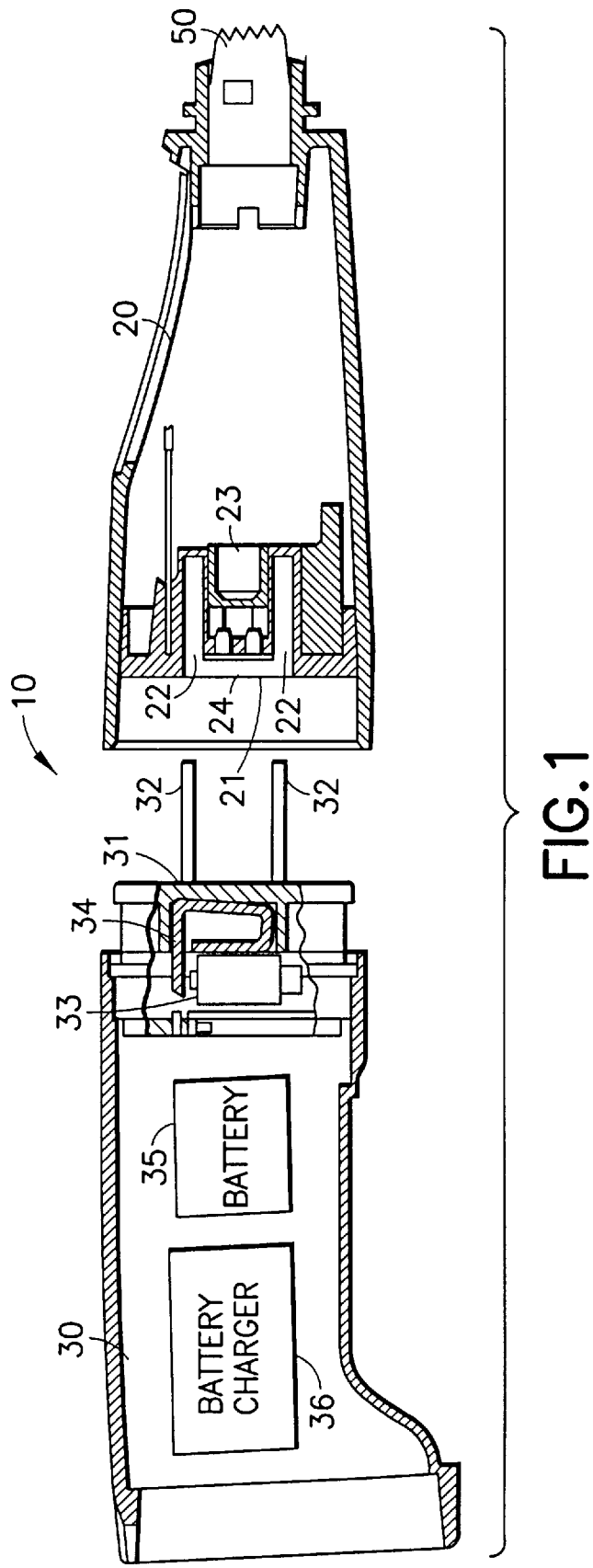
FIG. 1 is a cross sectional view in part and a block diagram in part of a cordless modular power tool embodying the present invention.
Figure 2:
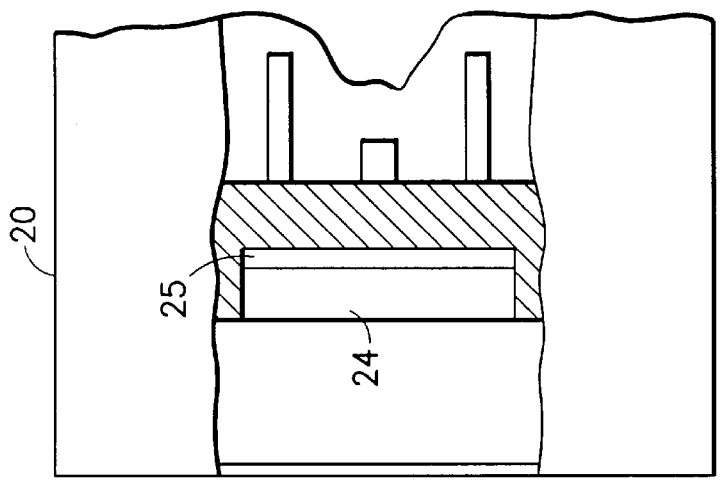
FIG. 2 is an exploded view of switch and switch actuator parts situated in the battery and motor modules of FIG. 1.

Referring to FIGS. 1 and 2, a cordless modular tool 10 embodying the invention is shown to have a motor module 20 containing a d.c. motor 23, a battery module 30 containing a battery 35 and a tool module 50. The battery module contains a first plug unit 31 with male electrical terminals 32 and the motor module contains mating second plug unit 21 with female electrical terminals 22. The first and second plug units are intended to be plugged together for operation as a power tool, such that the battery 35 supplies d.c. current via terminals 32 and 22 to motor 23. This mode is referred to herein as the d.c. mode. When unplugged, first plug unit 31 is operable in the a.c. mode to conduct a.c. current supplied from an a.c. power main (for example, a typical a.c. wall receptacle) to charge battery 35. First and second plug units 31 and 21 are illustrated as male and female units, respectively. This is preferred so that first plug unit 31 can be directly plugged into a standard a.c. wall receptacle.

Figure 4:
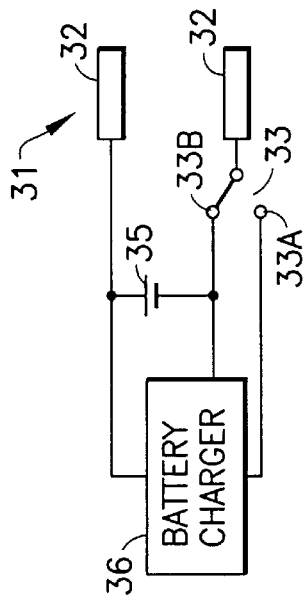
FIG. 4 is a circuit diagram in part and a block diagram in part illustrating the electrical connections of the electrical parts contained in the battery module.

Battery module 30 also contains a switch 33, a battery charger 36 and a circuit which interconnects switch 33, battery charger 36, battery 35 and first plug unit 31 for operation either in a d.c. mode or in an a.c. mode. This circuit is illustrated in FIG. 4 but not in FIG. 1 to avoid clutter. As shown in FIG. 4, switch 33 has first and second contact positions 33A and 33B, respectively. When connected to contact position 33B, switch 33 connects battery 35 to terminals 32 to provide d.c. current in the d.c. mode. When connected to contact position 33A, switch 33 connects the battery and battery charger to terminals 32 so as to receive a.c. current in the a.c. mode.

A means for placing first plug unit 31 in the a.c. and d.c. modes includes switch 33 and a switch actuator having a first actuator element 24 situated in motor module 20 and a second actuator element 34 situated in the battery module 30. Element 24 in the preferred embodiment is a permanent magnet of the rare earth type and element 34 is a piece of mild steel having good magnetic properties such as 1010 cold rolled steel. As best seen in FIG. 2, steel piece 34 is shaped with an actuator arm 34A arranged to activate the switch 33 and a portion 34B shaped, as for example, in a loop for rotational movement in cavity 37 formed in a part of battery module 30 adjacent first plug unit 31.

Figure 3:
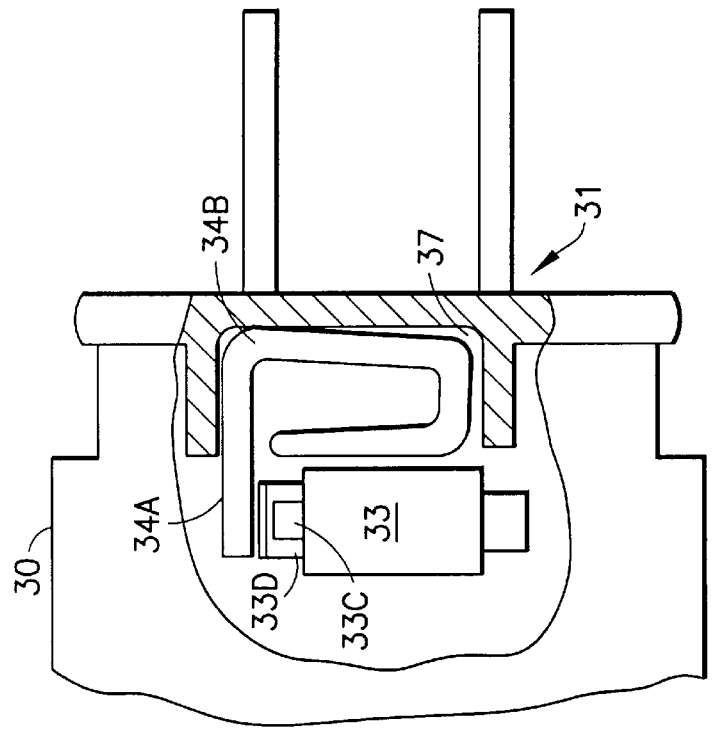
FIG. 3 is a partial view of the switch and switch parts situated in the battery module of FIG. 2 with the switch shown in its actuated or d.c. position.

Still with reference to FIG. 2, switch 33 is preferably a commercially available microswitch having a switch button 33C and a spring arm 33D for operating the switch button from a nonactuated position shown in FIG. 2 to an actuated position (see FIG. 3) corresponding to switch positions 33A and 33B in FIG. 4.

During the plugging process, as the battery and motor modules 30 and 20 come closer, the magnetic field of magnet 24 in the vicinity of steel piece 34 causes steel piece 34 to rotate in a counterclockwise direction, forcing spring steel arm 33D downward and depressing switch button 33C. This action places switch 33 in the actuated position or d.c.

mode. While plugged together, the magnetic field maintains steel piece 34 and spring arm 33D in the actuated position. During the unplugging process as the battery and motor modules separate, the magnetic field in the vicinity of steel piece 34 becomes weaker and eventually the force of spring arm 33D returns steel piece 34 in the clockwise direction to the unactuated position.

To enhance or focus the magnetic field, a concentrator 25 is placed behind magnet 24 in motor module 20 (best seen in FIG. 4). Concentrator 25 is preferably a mild steel having good magnetic properties such as 1010 cold rolled steel.

Tool 50 is shown only in part as its detail is not germane to the invention. The tool can be any moving instrumentality as for example, a saw, drill, toothbrush, flosser and the like.

Accordingly, there has been described a cordless modular power tool embodying the present invention. It is advantageous because the battery module has only a single plug unit that is used in both a d.c. mode to conduct d.c. current and in an a.c. mode to conduct a.c. current to charge the battery. Modifications can be made to the illustrated embodiment without departing from the spirit of the invention. Accordingly, the preferred embodiment is illustrative only and is not intended to limit the scope of the invention.

What is claimed is:

1. A cordless power tool having a battery module containing a battery, and a motor module containing a d.c. motor, the improvement comprising:

first and second mating plug units, each having two terminals, mounted on the battery and motor modules, respectively, the first mating plug unit comprising a pair of male terminals and the second mating plug unit comprising a pair of female terminals for receiving said male terminals; and means for placing the male terminals of the first plug unit (i) in an a.c. mode when unplugged from the second plug unit so as to be enabled to conduct a.c. current from an a.c. power main to charge said battery and (ii) in a d.c. mode when plugged to the second plug unit so as to be enabled to conduct d.c. current from the battery to the motor via the second plug unit terminals.

2. A cordless power tool according to claim 1 wherein said means for placing includes a switch and a switch actuator, operable as the battery and motor modules are being plugged and unplugged, to operate said switch to place the first plug unit terminals in the d.c. and a.c. modes, respectively.

3. A cordless power tool according to claim 2 and further comprising:

a circuit situated in the battery module and including a battery charger and said battery, switch and first plug unit terminals, said switch having (i) a first position to couple the battery, battery charger and first plug unit terminals to conduct a.c. current in the a.c. mode for charging of the battery and (ii) having a second position to couple the battery and the first plug unit terminals to conduct d.c. current in the d.c. mode.

4. A cordless power tool according to claim 3 wherein said switch actuator includes first and second elements situated in the motor and battery modules, respectively, said first and second elements coacting with one another during said plugging and unplugging process to operate said switch to place the first plug unit terminals in the d.c. and a.c. modes, respectively.

5. A cordless power tool according to claim 4 wherein the first actuator element is a permanent magnet that produces a magnetic force and the second actuator element is a metallic piece that responds to the magnetic force during the plugging and unplugging process and during the time the modules the battery and motor modules are plugged together to cause the switch to maintain the first plug unit terminals in the d.c. mode.

6. A cordless power tool according to claim 5 wherein the switch is a microswitch having a spring arm which coacts with the second element operable in the absence and presence of the magnetic force to maintain the switch in the first and second positions, respectively.

7. A cordless power tool according to claim 1 wherein the power tool is a power toothbrush.

8. The combination comprising:

a battery module containing a battery, a motor module containing a d.c. motor, first and second mating plug units, each having two terminals, mounted on the battery and motor modules, respectively, the first mating plug unit comprising a pair of male terminals and the second mating plug unit comprising a pair of female terminals for receiving said male terminals; and means for placing the male terminals of the first plug unit (i) in an a.c. mode when unplugged from the second plug unit so as to be enabled to conduct a.c. current from an a.c. power main to charge said battery and (ii) in a d.c. mode when plugged to the second plug unit so as to be enabled to conduct d.c. current from the battery to the motor via the second plug unit terminals.

9. The invention according to claim 8 wherein said means for placing includes a switch and a switch actuator, operable as the battery and motor modules are being plugged and unplugged, to operate said switch to place the first plug unit terminals in the d.c. and a.c. modes, respectively.

10. The invention according to claim 9 and further comprising:

a circuit situated in the battery module and including a battery charger and said battery, switch and first plug unit terminals, said switch having (i) a first position to couple the battery, battery charger and first plug unit terminals to conduct a.c. current in the a.c. mode for charging of the battery and (ii) having a second position to couple the battery and the first plug unit terminals to conduct d.c. current in the d.c. mode.

11. The invention according to claim 10 wherein said switch actuator includes first and second elements situated in the motor and battery modules, respectively, said first and second elements coacting with one another during said plugging and unplugging process to operate said switch to place the first plug unit terminals in the d.c. and a.c. modes, respectively.

12. A cordless power tool according to claim 11 wherein the first actuator element is a permanent magnet that produces a magnetic force and the second actuator element is a metallic piece that responds to the magnetic force during the plugging and unplugging process and during the time the modules the battery and motor modules are plugged together to cause the switch to maintain the first plug unit terminals in the d.c. mode.

13. The invention according to claim 12 wherein the switch is a microswitch having a spring arm which coacts with the second element operable in the absence and presence of the magnetic force to maintain the switch in the first and second positions, respectively.

* * * * *